US012690810B2

(12) United States Patent
Vallittu

(10) Patent No.: US 12,690,810 B2
(45) Date of Patent: Jul. 28, 2026

(54) IMPLANT FOR MONITORING OSSEOINTEGRATION AFTER IMPLANTATION

(71) Applicant: SKULLE IMPLANTS OY, Turku (FI)

(72) Inventor: Pekka Vallittu, Kuusisto (FI)

(73) Assignee: SKULLE IMPLANTS OY, Turku (FI)

( * ) Notice: Subject to any disclaimer, the term of this patent is extended or adjusted under 35 U.S.C. 154(b) by 297 days.

(21) Appl. No.: 18/282,364

(22) PCT Filed: Mar. 15, 2022

(86) PCT No.: PCT/FI2022/050165
§ 371 (c)(1),
(2) Date: Sep. 15, 2023

(87) PCT Pub. No.: WO2022/195165
PCT Pub. Date: Sep. 22, 2022

(65) Prior Publication Data
US 2024/0164710 A1 May 23, 2024

(30) Foreign Application Priority Data

Mar. 15, 2021 (EP) ...................................... 21162550

(51) Int. Cl.
*A61F 2/46* (2006.01)
*A61B 5/00* (2006.01)
(Continued)

(52) U.S. Cl.
CPC .......... *A61B 5/4851* (2013.01); *A61B 5/0002* (2013.01); *A61B 5/686* (2013.01);
(Continued)

(58) Field of Classification Search
CPC .......... A61B 5/4851; A61B 2034/2048; A61B 2034/2065; A61B 2034/254;
(Continued)

(56) References Cited

U.S. PATENT DOCUMENTS

2003/0040806 A1 2/2003 MacDonald
2003/0069644 A1 4/2003 Kovacevic et al.
(Continued)

FOREIGN PATENT DOCUMENTS

JP 53-23193 A 3/1978
JP 2008534140 A 8/2008
(Continued)

OTHER PUBLICATIONS

International Preliminary Examining Authority, PCT/FI2022/050165, mailed Jul. 3, 2023, 13 pages.
(Continued)

*Primary Examiner* — Jon Eric C Morales
(74) *Attorney, Agent, or Firm* — Timothy H. Van Dyke; Wolter Van Dyke Davis, PLLC

(57) ABSTRACT

The present invention relates to an implant (1, 30, 50, 70) comprising a non-metallic structural part (4, 38, 73) made of a fibre reinforced composite and having isoelastic properties with bone. The implant also comprises a first reference stress level sensor (6, 31, 51, 76) arranged in connection with the structural part, and a second osseointegration level sensor (7, 32, 52, 77) arranged on a surface of the structural part and capable of becoming attached to the bone during osseointegration of the implant.

14 Claims, 4 Drawing Sheets

(51) Int. Cl.
  *A61B 34/00* (2016.01)
  *A61B 90/00* (2016.01)

(52) U.S. Cl.
  CPC ........ *A61B 90/06* (2016.02); *A61B 2560/045*
    (2013.01); *A61B 2560/0462* (2013.01); *A61B*
    *2562/0247* (2013.01); *A61B 2562/0261*
    (2013.01); *A61B 2562/028* (2013.01)

(58) Field of Classification Search
  CPC ........ A61B 2090/364; A61B 2562/028; A61B
    34/25; A61B 5/0002; A61B 5/0031; A61B
    5/01; A61B 5/03; A61B 5/076; A61B
    5/145; A61B 5/14507; A61B 5/14532;
    A61B 5/14539; A61B 5/4528; A61B
    5/742; A61F 2/4657; A61F 2/4684; A61F
    2002/4666; A61F 2/38; A61F 2/3859;
    A61F 2/389; A61F 2/4455; A61F 2/4611;
    A61F 2/488; A61F 2002/30133; A61F
    2002/3067; A61F 2002/30673; A61F
    2002/30878; A61F 2002/4632; A61F
    2002/4633; A61F 2230/0015; A61F
    2250/0002

See application file for complete search history.

(56) References Cited

U.S. PATENT DOCUMENTS

| | | | |
|---|---|---|---|
| 2008/0065225 A1* | 3/2008 | Wasielewski | A61B 5/742 |
| | | | 623/18.11 |
| 2014/0277535 A1 | 9/2014 | Metzger et al. | |
| 2016/0000570 A1 | 1/2016 | Thuliez et al. | |
| 2019/0192198 A1 | 6/2019 | Janna et al. | |
| 2020/0297513 A1 | 9/2020 | Zellmer et al. | |

FOREIGN PATENT DOCUMENTS

| | | | |
|---|---|---|---|
| JP | 2016525389 A | 8/2016 | |
| JP | 2019-41886 A | 3/2019 | |
| WO | 20060105098 A3 | 10/2006 | |
| WO | 20140209916 A1 | 12/2014 | |

OTHER PUBLICATIONS

Bouillaguet, Serge et al., "Hydrothermal and Mechanical Stresses Degrade Fiber-Matrix Interfacial Bond Strength in Dental Fiber-Reinforced Composites", InterScience, 2005, pp. 98-108.

Zhao, D.S. et al., "Development of a multi-component fiber-reinforced composite implant for load-sharing conditions", Medical Engineering & Physics, 2009, vol. 31, pp. 461-469.

023P0006F Notice of reasons for refusal, 2023-555273, 11 pages.

Notice of Deficiencies for IL Patent Application 305792 mailed Jun. 8, 2024, 6 pages.

* cited by examiner 54
53
51
50
52
53'

S 60
61
62

T

IMPLANT FOR MONITORING OSSEOINTEGRATION AFTER IMPLANTATION

FIELD OF THE INVENTION

The invention relates to an implant, which is especially useful in orthopaedic surgery. The invention also relates to an implant system comprising the present implant.

BACKGROUND

An orthopaedic implant is a medical device manufactured to replace a missing joint or bone or to support a damaged bone. These implants are typically made of metals and are designed to retain function of the damaged part of skeleton. Although implants used today can have good success even in long term, implants can also sometimes lead to complications. For instance, it has been reported that up to 10% of peritrochanteric orthopaedic repairs fail due to fixation failures. Similar problems have also been encountered with total knee replacement implants, especially for the tibial component of the implant.

Stress-shielding and overloading is believed to be due to a mismatch of modulus of elasticity of the metals used in implants (titanium-vanadium has a modulus of elasticity of 120 GPa, cobalt-chromium 210 GPa) versus considerably lower modulus of elasticity of bone (typically 10-20 GPa, depending on the bone and part of the bone).

For bone repair implants, the most severe complication is indeed loosening of the implant. The loosening of an implant from surrounding bone can be an aseptic loosening due to stress shielding and overloading of the surrounding bone, or it can be due to peri-implant infections. For the diagnosis of the implant loosening, medical imaging technologies can be used. However, even with the high precision medical imaging systems, the very early stages of implant loosening cannot be detected. Another potential problem is an implant failure by fracture or delamination, which may be controlled radiologically or by sensors within the implant.

Some attempts to test possibilities for incorporation of sensors for detecting in vivo pathological processes of tissues have been made but many challenges of new technologies have been faced. For systems with complex electronics, the power consumption, size and robustness of the system as well as cost have limited the development of implants which could provide information of the surrounding tissues and integration, such as osseointegration of the implant to tissues. Another group of challenges with sensors relate to the stiff implant structure of high modulus of elasticity materials and incorporation of the sensors to the implant structures. The stiff implant structure does not allow the metal implant to bend or strain by physiological loading, i.e. under the influence of body-weight and normal movement. Because of this, currently used structurally stiff metal implants cannot be monitored to observe the different regions of the implant and their possibly different stress levels. Furthermore, metal implants do not allow free transmission of signals in the radio frequencies, due to the effect of Faraday's cage.

Document US 2019/192198 presents an orthopaedic fixation device including an inner core and a shaft formed of a multi-layered, fibre-reinforced composite. A sensing element is embedded within the multi-layered, fibre-reinforced composite. In this device, the sensing element is thus embedded within the device, and therefore cannot become attached to the bone during osseointegration. Furthermore, the sensing element is used to sense the condition of the fixation device itself, i.e. of the delamination of the fibre-reinforced composite.

OBJECTS AND SUMMARY OF THE INVENTION

An object of the present invention is to provide an implant that does not have the above-listed drawbacks, or at least, at least some of those disadvantages are reduced. Specifically, an object of the present invention is to provide an implant, for example a hip implant, a knee implant or a spinal implant, which can be continuously monitored and the integration of which to the surrounding environment can be efficiently and reliably monitored throughout the lifetime of the implant. A further object is to provide an implant allowing osseointegration after implantation to be monitored, and which osteolysis, i.e. loosening, can also be detected at an early stage. A still further object is to provide an implant for which it is possible to also monitor the state of the surrounding tissues for signs of inflammation or infection. A still further object is to provide an implant having isoelastic properties with bone surrounding the implant, when in use.

A typical implant according to this description comprises
- a non-metallic structural part made of a fibre reinforced composite, having isoelastic properties with bone,
- a first reference stress level sensor arranged in connection with the structural part, and
- a second osseointegration level sensor arranged on a surface of the structural part and capable of becoming attached to the bone during osseointegration of the implant.

A typical implant system according to this description comprises
- an implant as described in this description, and
- at least one processing core and memory comprising computer executable instructions,
the computer executable instructions being configured to, together with the memory and the at least one processing core, cause the implant system to process the measurement results received from the sensors.

DETAILED DESCRIPTION OF THE INVENTION

Figures 1, 2:
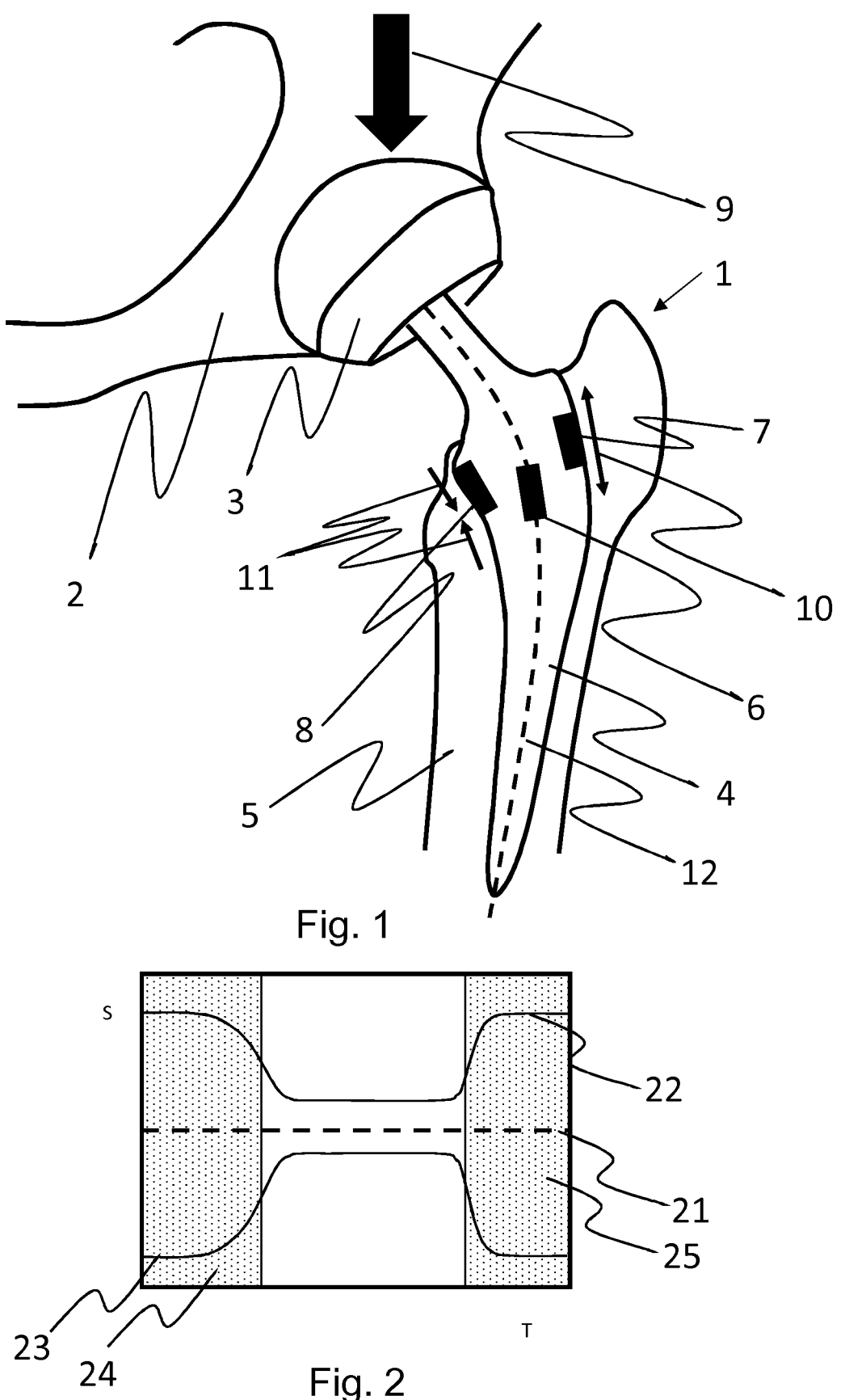
FIG. 1 schematically shows a hip implant according to a first embodiment.
FIG. 2 illustrates the stress levels at the various sensors in function of time for the hip implant according to the first embodiment.

In this specification, by curing it is meant polymerisation and/or crosslinking. By matrix, it is understood the continuous phase of a composition and by uncured matrix it is meant a matrix that is in its deformable state but that can be cured, i.e. hardened, to an essentially non-deformable state. The uncured matrix may already comprise some long chains but it is essentially not yet polymerised and/or crosslinked. In the present description, the polymerisation may be performed by any known way, such as autopolymerisation, light polymerisation, thermal polymerisation, ultrasound or microwave polymerisation. The curing of a resin leads to a composite material, wherein the cured resin forms the matrix.

The term implant is used in this text as a general term, describing various implantable devices such as prostheses, bone attachment plates etc.

By isoelasticity, it is meant materials having a modulus of elasticity similar to the human bone. The modulus of elasticity is considered to be 14.8 GPa for trabecular bone and 20.7 GPa for cortical bone. For example, isoelasticity may mean that the modulus of elasticity is within +/−25%, +/−10% or +/−5% of the modulus of elasticity of the bone where the implant is arranged. A glass fibre-reinforced composite may have a modulus of elasticity within the range of that for cortical bone. For example, a continuous unidirectional glass fibre-reinforced composite having a thermoset polymer matrix is known to have a modulus of elasticity of 25.5 GPa, where the modulus of elasticity is believed to be related to the fibre fraction (*J Biomed Mater Res* 2006; 76:98-105). Modelling and animal studies have shown the isoelastic behaviour of fibre-reinforced composite materials with bone (*Med Eng Phys* 2009; 31:461-469).

A typical implant according to this description comprises
a non-metallic structural part made of a fibre reinforced composite, having isoelastic properties with bone,
a first reference stress level sensor arranged in connection with the structural part, and
a second osseointegration level sensor arranged on a surface of the structural part and capable of becoming attached to the bone during osseointegration of the implant.

The implant according to this description thus takes advantage of a combination of non-metallic implant material, i.e. the implant is made of fibre reinforced composite, for example, and properly arranged sensors that measure the stress exercised on the implant. The stress may be compression or traction, for example. The implant thus comprises a non-electromagnetic shielding material having isoelastic properties with bone and containing at least two sensors inserted to detect levels of stress in the implant. The stress levels give information of osseointegration, i.e. how well and when the implant is attached to the surrounding bone, after implantation. Once the implant is attached to the bone, a change is the stress levels indicates osteolysis, i.e. detachment of the implant from the bone. The sensors can be read wirelessly and thus allow an easy and safe way of monitoring the state of the implant, while allowing early detection of loosening of the implant. As explained above, the loosening is believed to be cause by different stresses exercised on the osseointegrated sensor and in the implant at its various places, combined to the fact that the implant material has a different elastic modulus than the bone. In this description, the fibre-reinforced composite is isoelastic with the bone. This means that the composite is designed for each particular use, as the elastic properties of bones vary depending on the bone and sometimes even the part of a given bone. The implant may also be designed to be in contact with soft tissue, in which case the stress levels vary in function to the elastic properties of the soft tissue. The implant can thus be any bone repairing implant such orthopaedic, spinal, cranial, maxillofacial or plastic surgery implant.

The sensors are thus typically positioned in or on the implant at locations of different levels of stress e.g. the lowest level of physical stress (neutral axis) and the highest level of stress (surface) and by comparing signals from the sensors it is possible to monitor how well the implant itself is carrying the load by the body weight and how the surrounding bone structures are taking the load to be carried via osseointegration. That is, when the implant itself is straining, bending or compressing with good attachment to the adjacent bone, the signals are different than when the implant is still in a bone healing phase, or a previously integrated implant has become loose. On the other hand, the sensor on the surface of the implant itself monitors its stress level based on the level of osseointegration to the bone. Stress of the osseointegrated sensor can be tension, compression, shear or any of their combinations.

The implant (also referred to as "implant" in this description) thus comprises at least two sensors, which are both stress sensors. The first sensor, called a first reference stress level sensor (which can be also referred to as "first sensor" for sake of brevity in this description), is arranged either inside the structural part or on its outer surface, depending on the application, i.e. type of implant. This first sensor gives the reference level, to which the second sensor's measurements are compared to. In case the first sensor is arranged inside the structural part, is it typically arranged on a central axis of the structural part, at a location where the stress exercised on the implant does not change in function of time, osseointegration and/or osteolysis. In such cases, the measurement of the stress from the first sensor is essentially constant. In some other cases, for example for spinal cage implants, the first reference sensor may have a slightly different function, which is explained in more detail below. The reference stress level sensor may thus also be arranged on the surface of the implant, depending on the type of implant.

The implant also comprises a second osseointegration level sensor (also called "second sensor" in this description, for reasons of brevity), which is arranged on the surface of the structural part. Depending on the implant, the second sensor is arranged at a location where the level of stress varies depending on whether the implant is attached to the bone or not. In addition, the second sensor is intended to monitor its level of osseointegration. Therefore, the exposed surface of the second sensor is bioactive in the same manner as the surface of the implant body.

Both the first sensor and the second sensor, as well as any optional further sensors are preferably configured to transmit measurement results wirelessly. Ideally, both sensors are also such that they do not need an external power source, or they include a power source that can be expected to last the lifetime of the implant. Naturally, all the components of the implant must be biocompatible. In some embodiments, the stress sensors are powered wirelessly during the read-out of their measurement results. For example, the stress sensors may comprise near-field communication (NFC) or radiofrequency identification (RFID) capability to enable provision of the measurement results, and, optionally, also wireless powering of the sensors. Further examples of wireless communication technologies applicable to stress sensors in various embodiments include Bluetooth™ and Bluetooth-Low Energy™ (BTLE).

Preferably, the implant and the second sensor attaches to the bone both by physical and chemical interactions. Physical attachment is typically based on surface roughening of the implant, creating friction with bone to create attachment. Chemical attachment typically requires the use of bioactive component(s) for the implant. Typically, such coatings of implants comprise bioactive glasses of particles or sol-gel coatings. Other common bioactive compounds are calcium phosphates such as hydroxyl apatite, tricalcium phosphates and calcium carbonates. The fibre reinforced composite is preferably designed to have the same modulus of elasticity than cortical bone, i.e. it is isoelastic with cortical bone. In addition, the design of the implant preferably simulates the structure of skeleton. Due to these aspects, stress applied to the bone, for instance when walking, is transferred to the isoelastic implant via the bone bonding interface, and the implant functions similarly to natural bone and joints. Thus, during osseointegration of the implant to the adjacent bone, the levels of stress in the implant and sensors changes with time. The same applies if osteolysis, i.e. loosening of the implant takes place. In at least some embodiments, the second sensor is arranged to measure stress in a direction that is parallel to a length axis of the implant at the part of the implant where the second sensor is attached.

According to an embodiment, the implant further comprises a third sensor, arranged on the surface the structural part. The third sensor is also configured to transmit measurement results wirelessly. The third sensor may be an additional stress sensor or a biochemical sensor, such as a pH sensor which measures pH in the implant and/or sensor—bone interface as an indicator of osteolysis or other physiological or pathological processes. The third sensor may be arranted diametrically opposed to the second sensor, especially if it is an additional stress sensor.

When three sensors are used, this allows measuring bending strain, osseointegration and pH on the implant at different locations of the implant and bone-implant interface. After being integrated to the bone (i.e. after osseointegration of the implant), the isoelastic implant begins to strain as the adjacent part of bone and skeleton strains the implant, when loaded by body weight and movement. When the bone has healed and implant is osseointegrated, the pH at the implant surface is typically 7.35-7.45.

According to an embodiment, the second osseointegration level sensor and the optional third sensor is a sensor for monitoring biochemical reactions in the peri-implant tissues.

The stress level sensor may be selected from a group consisting of stress gauge, microelectromechanical sensor (MEMS), piezoresistive sensor and passive resonator-based sensor. Preferably the sensors are wireless and function without a battery or other external energy source, and also do not need any electrical connections. Typically, the sensors are also small in size. The sensor may also be an antenna-SAW-resonator system (SAW=surface acoustic wave). The sensor can be covered with a coating of for example sapphire, aluminium oxide or diamond-like carbon. The coating may be applied for example by atomic layer deposition (ALD). The diamond-like carbon coating may be a nano-coating. The coating is used for hermetic sealing and bio-compatibility with an additional bioactive coating.

As mentioned above, even with the high precision medical imaging systems, the very early stages of implant loosening cannot be detected, although early signs of implant loosening would be detectable by implant-bone contact and attachment observation or by detecting molecular markers and/or pH changes as signs of local inflammation or infection reactions. As it is however preferable to be able to detect loosening of an implant at an early stage, before further damage to the surrounding bone, further solutions to these problems are needed. Indeed, when an implant becomes loose, the risk of infection increases, and infection can make the later replacement surgery significantly more difficult.

Therefore, according to another embodiment, the implant further comprises a biochemical sensor, such as a pH sensor arranged on the surface of the structural part, the biochemical sensor being configured to transmit measurement results wirelessly. Indeed, one or more sensors can be used to detect and measure also other parameters than physical stress which relate to the bone healing and implant attachment or loosening. For example, the biochemical sensors may monitor pH at the implant interface, or for example the presence of specific biomarkers indicating e.g. macrophage activity. When the implant becomes loose aseptically or due to microbial infection, the pH of the tissue drops from the physiological level (7.35-7.45) to acidic (6.8-6.9). The pH change can thus be used as additional information in implant diagnostics. The pH sensor can be a hydrogel based sensor as it does not require external power sources for measuring chemical stimuli such as pH, ions, antigens, temperature and glucose. The hydrogel sensor may also give information of the level of ossification or signs of microbial infections which are important, especially in cranial implants. Monitoring of the hydrogel of the biochemical sensor can be made wirelessly by using ultrasound. The ultrasonic waves reflected at the sensor interface may be captured by transmitting transducer connected to an oscilloscope.

According to an embodiment, the implant is a fracture fixation plate, a stem of a hip prosthesis, a hip prosthesis, a knee prosthesis, an intramedullary nail, a vertebral fusion implant, plastic surgery implant, a jawbone implant, a cranial implant, a dental implant or a distractor. A vertebral fusion implant may also be called a spinal fusion cage.

Simple every day activities such as walking, running and in particular, rising up from a seated position result in different force vectors to the implant-bone system. For a hip implant, the trabecular bone which is closest to the implant surface supports 54% of the total load in human proximal femur and 46% of the load is carried by the cortical bone. The type, location and magnitude of stress vary in different parts of the implant-bone structure. For example, in femur the medial side is subjected to compression stress whereas the lateral side is subjected to tensile stress in an axial loading.

In vertebral fusion implant surgery one of the most significant clinical challenges following insertion of spine fusion cage implants is determining when solid bony fusion has occurred. Forces on the spine are high and dynamic with muscle contraction forces exceeding 4.7× body weight. Therefore, all information for the implant which indicates load sharing of the implant itself is valuable for defining the timing of begin of normal everyday life after the surgery.

Osteoarthritis of the knee is a common musculoskeletal pathology, which is surgically treated by total knee arthroplasty. In the total knee arthroplasty, the distal femur bone and proximal tibia are resected and replaced with implants typically having a polyethylene articulate component. The implant is loaded with forces of about 1.8-2.6× body weight when walking and 4× body weight when jogging. Although complication rate of total knee arthroplasty is relatively low, loosening of the implant is sometimes observed, and it would thus be beneficial to be able to monitor also knee implants closely.

For cranial implants, it may be necessary to monitor whether the implant, once in place, receives any hits or impacts that might affect the implant. The present sensors can be used for this purpose. Similarly, the effect of an infection or inflammation on a cranial implant is beneficial to be monitored, too.

According to a specific embodiment, the implant is a hip prosthesis, wherein the first structural part is femoral stem, the first reference stress level sensor is arranged inside the femoral stem, on the axis of the femoral stem, the second osseointegration level sensor is arranged on the surface of the femoral stem, on its lateral side, and an optional third osseointegration level sensor is arranged on the surface of the femoral stem, on its medial side.

Such hip prosthesis may further also comprise a second structural part which is an acetabular cup.

According to another specific embodiment, the implant is an intervertebral disc, wherein the first reference stress level sensor is arranged on a first surface of the structural part, the first surface being a lateral distal surface of the structural part, and the second osseointegration level sensor is arranged on a second surface of the structural part, the second surface being arranged to face a vertebral body.

The lateral distal surface is thus, when the implant is in place and the patient is standing, the surface that is essentially vertical and facing towards the back of the person's body. The second surface is in this situation a horizontal surface.

According to a still further specific embodiment, the implant is a knee prosthesis, wherein the first structural part is tibial component comprising a tibial base plate, and a tibial stem, the tibial stem defining a tibial axis, the first reference stress level sensor is arranged on the surface of the tibial stem, essentially parallel to the tibial axis, the second osseointegration level sensor is arranged on the surface of the tibial base plate, the surface being essentially perpendicular to the tibial axis, on a lateral side, facing away from the tibial base plate, and an optional pH sensor is arranged on the surface of the tibial base plate, the surface being at an angle different from 90° with respect to the tibial axis.

In this embodiment, the knee prosthesis may also comprise a second structural part which is a femoral component and a third structural part which is a spacer.

The structural part of the implant may have a uniform structure, or it may have a structure that imitates the bone or joint that it replaces. For example, for a hip prosthesis, the femoral stem may have as its core, a relatively thin metallic part, which has isoelastic properties with bone. Preferably, the structural part of the implant has uniform structure and uniform properties. The surface of the implant may be either porous or non-porous, wherein non-porous means a material that is essentially impermeable to fluids present in the site of implantation. In case the surface layer is porous, i.e. perforated (either due to its material or after a specific perforation step during its manufacture), its porosity for example such that its average pore size is 0.8-500 micrometres. The surface of the implant, up to a certain depth within the implant (such as 0.5-5.0 mm from the surface of the implant towards its core) may be porous, having a continuous porosity for example with an average pore size of 100-1000 micrometres. The porosity is such that extracellular fluids and cells can penetrate the porous part and allow ingrowth of bone, blood cells and other tissues. An optimal pore size for endosseus applications is 100 to 500 micrometres when bone ingrowth is considered, but the porous part may optionally also contain larger holes.

The implant's structural part may be manufactured for example by sintering, laser sintering, moulding suitable material, electrospinning, 3D printing, filament winding, laminating or by milling. According to an embodiment, the production technologies of these implants are based on use of digital technologies and additive manufacturing processes, such as laminating layers of fibre reinforced composites to optimally simulate the structure and mechanical requirements of bone.

An optimal isoelastic material for the implant is fibre reinforced composite. Preferred reinforcing fibres are non-metallic fibres of glass, carbon, graphite, polyethylene, aramid, polystyrene or rigid rod polymers (RRP). The matrix is preferably a biostable polymer matrix of acrylate, epoxy, polyether ketone (PEEK), polyethylene (PE) or polyester. Other suitable materials are listed below.

One suitable example of bioactive glass to be used in the implant material is the glass S53P4, which is a resorbable bioactive glass with the composition of 53% $SiO_2$, 23% $Na_2O$, 20% CaO and 4% $P_2O_5$ (available for example from BonAlive Biomaterials Ltd in Turku, Finland). It may be particularly useful on the surface of the implant, to allow good attachment to bone.

The fibres may be any suitable fibres known per se, for example selected from the group consisting of inert glass fibres, silica/quartz fibres, carbon/graphite fibres, inert ceramic fibres, aramid fibres, zylon fibres (which are rigid rod polymer fibres), polyethylene fibres, polytetrafluoroethylene fibres, such as Teflon® fibres, poly(p-phenylene-2,6-benzobisoxazole) fibres, poly(2,6-d iimidazo(4,5-b4',5'-e) pyridinylene-1,4(2,5-dihydro)phenylene fibres, polyolefin fibres, fibres prepared from copolymers of olefins, polyester fibres, polyamide fibres and mixtures thereof. Poly(p-phenylene-2,6-benzobisoxazole) fibres and poly(2,6-diimidazo (4,5-b4',5'-e)pyridinylene-1,4(2,5-dihydro)phenylene fibres belong to a group called rigid-rod polymer fibres. It is obvious to a person skilled in the art that any other known fibres may be used in the present invention, provided that it is possible to obtain a suitable adhesion between said fibres and matrix, in order to achieve the desired mechanical properties and that the fibres are biocompatible.

According to one embodiment of the invention, the fibres are selected from the group consisting of inert glass fibres. According to another embodiment, the glass fibres are made of a glass composition of E-glass, S-glass, R-glass, C-glass or bioactive glasses.

According to yet another embodiment, the diameter of the fibres is 4-25 μm. The diameter of the fibres can be for example from 3, 5, 6, 10, 15, 20, 25, 30, 40, 45, 50, 60, 70 or 80 μm up to 5, 6, 10, 15, 20, 25, 30, 40, 45, 50, 60, 70, 80, 90 or 100 μm. Fibres in the nanometre scale, i.e. with a cross-sectional diameter varying between 200-1000 nm can also be used.

The fibres may be in the form of fibre fabrics or fibre mats, and they may be oriented in two directions, three directions, four directions or randomly thereof.

The matrix of the composite may be made of a resin consisting of monomers selected from the group consisting of methyl acrylate, ethyl acrylate, propyl acrylate, isopropyl acrylate, n-hexyl acrylate, styryl acrylate, allyl acrylate, methyl methacrylate, polymethyl methacrylate, ethyl methacrylate, propyl methacrylate, isopropyl methacrylate, n-butyl methacrylate, isobutyl methacrylate, 2-ethylhexyl methacrylate, cyclohexyl methacrylate, isobornyl methacrylate, tetrahydrofurfuryl methacrylate, benzyl methacrylate, morpholinoethyl methacrylate, diurethane di methacrylate, acetoacetoxy ethyl methacrylate (AAEM), methacrylate functionalized dendrimers, other methacrylated hyperbranched oligomers, hydroxymethyl methacrylate, hydroxymethyl acrylate, hydroxyethyl methacrylate, hydroxyethyl acrylate, hydroxypropyl methacrylate, hydroxypropyl acrylate, tetrahydrofurfuryl methacrylate, tetrahydrofurfuryl acrylate, glycidyl methacrylate, glycidyl acrylate, triethylene glycol diacrylate, tetraethylene glycol dimethacrylate, tetraethylene glycol diacrylate, trimethylolethane trimethacrylate, trimethylolpropane trimethacrylate, pentaerythritol trimethacrylate, trimethylolethane triacrylate, trimethylolpropane triacrylate, pentaerythritol triacrylate, pentaerythritol tetramethacrylate, pentaerythritol tetraacrylate, ethylene dimethacrylate, ethylene diacrylate, ethylene glycol dimethacrylate, diethylene glycol dimethacrylate, triethylene glycol dimethacrylate (TEGDMA), ethylene glycol diacrylate, diethyleneglycol diacrylate, butylene glycol dimethacrylate, butylene glycol diacrylate, neopentyl glycol dimethacrylate, hydroxyethyl methacrylate, urethan dimethacrylate, starburst methacrylated polyesters, hyperbranched methacrylated polyesters, neopentyl glycol diacrylate, 1,3-butanediol dimethacrylate, 1,3-butanediol diacrylate, 1,4-butanediol dimethacrylate, 1,4-butanediol diacrylate, 1,6-hexanediol dimethacrylate, 1,6-hexanediol diacrylate, di-2-methacryloxyethyl-hexametylene dicarbamate, di-2-methacryloxyethyl-trimethylhexametylene dicarbamate, di-2-methacryloxyethyl-dimethylbenzene dicarbamate, di-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-tri methyl hexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-tri methyl hexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-tri methyl hexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl-4-cyclohexyl carbamate, 2,2-bis(4-(2-hydroxy-3-methacryloxy)phenyl)propane (BisGMA), 2,2'-bis(4-methacryloxyphenyl)propane, 2,2'-bis(4-acryloxyphenyl)propane, 2,2'-bis[4(2-hydroxy-3-acryloxyphenyl)propane, 2,2'-bis(4-methacryloxyethoxyphenyl)propane, 2,2'-bis(4-acryloxyethoxyphenyl)-propane, 2,2'-bis(4-methacryloxypropoxyphenyl)propane, 2,2'-bis(4-acryloxypropoxyphenyl)propane, 2,2'-bis(4- methacryloxydiethoxyphenyl)-propane, 2,2'-bis(4-acryloxydiethoxyphenyl)propane, 2,2'-bis[3(4-phenoxy)-2-hydroxypropane-1-methacrylate]propane, 2,2'-bis[3(4-phenoxy)-2-hydroxypropane-1-acrylate]propane, polyetheretherketone and mixtures thereof.

The matrix may naturally also consist of a mixture of a monomer(s) and polymer(s).

According to one embodiment, the matrix material is an acrylate polymer. According to another embodiment, the matrix resin is selected from the group consisting of substituted and unsubstituted dimethacrylates and methacrylates. Some especially advantageous matrix materials (monomers) are methyl acrylate, methyl methacrylate, methacrylate functionalized dendrimers, glycidyl dimethacrylate (bis-GMA), triethylene glycol dimethacrylate (TEGDMA) and urethane dimethacrylate (UDMA). The materials may be used as blends and they may form interpenetrating polymer networks (IPNs). They may also be functionalised with bioactive molecules that allow for a drug-like contact effect. Combinations of monomers and polymers are also suitable to be used, including modifications of resin systems by antimicrobial side group containing iodine which offers additional benefit in increasing radio opacity of the resin system.

The implant and the osseointegrated sensor may further comprise modifier particles in the porous part if one is present on the surface. These modifier particles may for example be bioactive and for example improve the osteoconductivity, osteoinduction and osseointegration of the implant and surface locating stress sensor. The particles may be in the form of particulate fillers or fibres. According to one embodiment, the modifier particles are selected from the group consisting of bioactive ceramics, silica gel, titanium gel, silica xerogel, silica aerogel, natrium silica glass, titanium gels, bioactive glass ionomer, Ca/P-doped silica gel and mixtures thereof. Any combination of said materials may naturally also be used.

The implant may yet further comprise additional particulate filler material, such as metal oxides, ceramics, polymers and mixtures thereof. Metal oxides may for example be used as radio or X-ray opaque materials or as colouring materials. Care should be exercised when selecting the filler materials, not to hinder the transmission of signals from the sensors.

The porous surface part of the implant, if present, may also comprise therapeutically active agents or cells such as stem cells, proteins such as growth factors and/or signalling molecules. Several kinds of cells including hematopoietic bone marrow cells, fibroblasts, osteoblasts, regenerative cells, stem cells, like embryonic stem cells, mesenchymal stem cells or adipose stem cells can be seeded to the implant. The embryonic stem cells may or may not be of a human origin. Stem cells seeded to the implant can be cultured in bioreactors ex vivo, in other parts of the body before inserting the formed tissue into its final place, or directly at the place where regenerative and reconstructive treatment is needed.

For receiving more detailed information of the implant and its attachment to the bone, the stress sensor(s) arranged on the surface may be covered with the same bioactive substance than the actual implant surface. Via bioactivity, the bone is attached to the implant and to the sensor surface and the sensor thus measures and transmits signals which can be even more reliably used to determine bone healing and bone attachment. Thus, when the implant and the sensor surface are loose form the bone, the level of stress varies from that with good bone attachment. Some suitable bioactive components to attach the sensors surface to the bone are bioactive glasses, bioceramics of calcium phosphates, apatites, calcium carbonates and bioactive sol-gel coatings.

The implant may be used for reconstitution of bones following a trauma, a defect or a surgery of diseases. Implant reconstruction of damaged or missing parts of skeleton is performed by providing immediate repair of an anatomical shape and adequate mechanical support of the remaining pieces of bone with simultaneous penetration of blood and bone forming cells from the adjacent tissues to the implant.

The present implant may also comprise a non-metallic structural part made of a fibre reinforced composite, having isoelastic properties with bone; and a sensor to detect biochemical reactions and markers in the peri-implant tissues. The sensor can be for example a pH sensor as described above. All the other embodiments and variants disclosed above apply mutatis mutandis to this kind of implant without a stress level sensor.

A typical implant system according to this description comprises an implant as described above,
at least one processing core and memory comprising computer executable instructions, the computer executable instructions being configured to, together with the memory and the at least one processing core, cause the implant system to process the measurement results received from the sensors.

The implant system may further comprise a wireless receiver configured to receive the measurement results wirelessly from the stress sensor(s) and, optionally, a wireless transmitter capable of powering the stress sensor(s) wirelessly using electromagnetic waves. In some embodiments, the implant system has a wired or wireless connection to a separate wireless transceiver capable of receiving the measurement results directly wirelessly from the stress sensor(s).

The at least one processing core and memory comprising computer executable instructions may be integrated in a single device, such as a monitoring device. For example, the single device may be a mobile device such as a mobile telecommunication device, which collects the data for a certain amount of time and transmits it to a database or similar at intervals of time. The monitoring device may also be for example integrated to clothes.

According to an embodiment, the at least one processing core and memory comprising computer executable instructions are integrated to a mobile device. The mobile device may be configured to transmit results of analysis to a database and to raise an alarm in case of change in the results of analysis. The analysis typically comprises comparing the data to previous data from the same implant, and the data can be sent to a medical care database.

The monitoring device can thus be a device which is used in hospitals for diagnostic purposes, a portable device or a device incorporated in smart clothes for providing real-time information of the implant's function when load bearing, e.g. during physical exercise.

Typically, the measurement results are transmitted as electromagnetic signals, the frequency of which may be dependent on the stress state of the sensor. The signals can be transmitted wirelessly using radio frequencies. Indeed, signal transfer from the sensor in the implant to a monitoring device may be made by exposing the part of the body where the implant is located to a radiofrequency field. Physical stress exercised on the implant may cause a change in capacitance or inductance of the sensor, which can then be detected using an external antenna of the monitoring device and transmitted further to a medical database or a data storage system in the patient's mobile phone. For allowing precise signal transfer from the implant, the implant material should not cause electromagnetic shielding or interference and thus it is at least mainly non-metallic. With biochemical sensors the signal transfer is made for example via ultrasound waves.

Some specific examples of how the sensors can be monitored are given below. For a hip implant, the femoral stem comprises in this example three stress sensor, located as illustrated in FIG. 1 below. The stress applied to the femoral stem and sensors of the implant when the patient is walking changes the sensor's free space resonant frequency, and this shift is associated with localised changes in their electric and magnetic fields as a consequence of the sensor's deformation. The three sensors of the femoral stem are different for their inductance and capacitance and they can therefore be distinguished by the monitoring device. The monitoring device is a network analyser system which is used for interrogating the sensors. A loop antenna transmits energy which excites resonant modes of the sensors and the antenna is used to receive the return response from the sensors.

For a cranial implant, the porous fibre reinforced composite framework of the implant may have a pH sensitive hydrogel sensor made of silica nanoparticles and acrylamide. After the implant has been osseointegrated, the pH in the implant and in the peri-implant tissues are in the level the physiological pH and it can be monitored through soft tissues with ultrasound transducer with predetermined resonant frequency using a function generator and a radio frequency amplifier. The ultrasonic waves reflected at the sensor interface can thus be captured by the transmitting transducer connected to an oscilloscope. When the implant is microbially infected, the peri-implant tissue pH drops which can be monitored and actions for antibiotic treatment are indicated.

The present description also relates to a method for monitoring the implant as described above, using the system described above, the method comprising receiving the measurement results of the sensors,
processing the measurement results received,
optionally transmitting results of analysis to a database, and
raising an alarm in case of change in the results of analysis.

When the implant has been inserted with friction attachment to the femoral bone and loaded, the implant behaves as a loose object and it is stressed only to a limited extent. At this stage, the signals from the sensors do not show any frequency shift. During osseointegration the stress begins to be transferred more from bone to the implant and the implant stem starts slightly to bend which causes tensile stress to the lateral surface and compression stress to the medial surface and this stress is observed by the frequency shift. The frequency shift of compared to the signals of baseline and to signals of the internal reference sensor (sensor at the neutral axis). The reverse is observed when osteolysis begins and the implant starts to loosen from the bone. In case the implant is also equipped with a pH sensor, it will be observed that pH starts dropping, which confirms the loosening of the implant. The level of signal difference will thus remain the same until the implant starts to loosen. Therefore, it is possible to monitor the attachment of the implant and in case loosening is observed, surgical or other medical corrective actions can be taken.

For a vertebral fusion implant as illustrated below in FIG. 5, a monitoring device at the doctor's office is used to follow the pressure change of the upper surface sensor compared to the reference sensor at the axial wall of the implant. Reduction of the surface pressure by the upper surface sensor indicates bony fusion to have taken place.

The present description further relates to a (non-transitory) computer readable medium comprising program instructions that, when executed by at least one processor, cause an apparatus to perform at least the steps of the method for monitoring the implant, as described above. Further, the present description relates to a computer program configured to cause a method as defined above, to be performed.

Some embodiments of the invention are explained in more detail in the enclosed drawing, which are not to be construed as limiting the claims. The reference signs are also not to be construed as limiting the claims.

EXPERIMENTAL PART

Example 1

Manufacturing of a Femoral Stem of Total Hip Prostheses with Sensors

A stem of a total hip implant replacement implant was fabricated from non-conductive continuous unidirectional S-glass fibre reinforced composite in a dimethacrylate resin matrix, with a fibre load or 68 wt-% of the total weight of the composite. The diameter of a single fibre was 15 μm and the resin matrix was a mixture of bisphenol A-glycidyl methacrylate (BisGMA) and triethylene glycol dimethacrylate (TEGDMA) monomers in a ratio of 70/30 with a photoinitiator system of camphorquinone and 2-(dimethylamino) ethyl methacrylate (DMAEM). The amount of the photoinitiator system was 0.7 wt-% of the total weight of the resin, and the two components were present in equal amounts. Femoral stem of the implant was made of continuous unidirectional glass fibres with surface layer of woven glass fibres for increasing torsional force resistance. Outermost surface of the implants was coated with particles of bioactive glass (S53P4) having an average particle size of 500 μm (ranging from 450 to 550 μm, measured by sieving) for bone attachment. During fibre laminations, a sensor array of three open-circuit sensors (passive resonator based sensors made of copper) were incorporated as follows. One of the sensors was placed in the middle of the stem (on an axis of the stem), one on the medial surface of the stem (compression side) and one on the lateral side of the stem (tension side), diametrically opposed to the sensor that was on the medial surface of the stem. The surface sensors were placed under a layer of woven glass fibre having a thickness of 0.06 mm for sensing the stress at the interface between the implant surface and the bone. An additional sensor which is sensitive to pH change was added close to the compression side or tension side sensor to complete the sensor array system.

Example 2

A cylindrical vertebral fusion implant was made of glass fibre reinforced composite tube (same materials as in Example 1) with a wall thickness of 1.5 mm. Fibre orientation in the tube was +/−45 degrees with respect to the long axis of the tube. The tube was milled for holes required by the instrumentation which is used to install the implant in place. The inner part of the tube was filled with particles of bioactive glass (S53P4, average particle size 500 μm, measured as in Example 1) for enhancing the solid bony fusion of vertebrae. The upper and lower part of the tube-like implant were covered with a perforated mesh-line glass fibre-reinforced composite laminate, the largest diameter of the perforations being 400 μm.

A first sensor was inserted to the long axial wall of the tubular implant for measuring shear stress on the wall and a second identical sensor was inserted to the perforated wall of the tube, to sense the surface pressure by the compression forces between the vertebrae. All the sensors used were passive resonator based sensors made of copper.

DETAILED DESCRIPTION OF THE DRAWING

FIG. 1 schematically shows a hip implant 1 according to a first embodiment. The hip implant 1 is attached to a hip 2 via acetabular cup 3. A femoral head (not visible) is arranged within the acetabular cup 3. A structural part 4 (attached to the femoral head), i.e. a femoral stem, is arranged within a femur 5 of the patient. A first stress level sensor 6 is arranged on the axis 12 of the femoral stem 4 to indicate a reference stress level. A second stress level sensor 7 is arranged on the surface of the femoral stem 4, on the side of it that is towards the side of the patient once the implant is in place, i.e. on the lateral side. A third stress level sensor 8 is arranged also on the surface of the femoral stem 4, but diametrically opposed to the second sensor 7, i.e. on the side that is towards the inner thigh of the patient once the implant is in place, i.e. on the medial side.

The arrows illustrate the direction of force that is exercised on the hip implant when in use, i.e. when the patient moves or stands. The arrow 9 shows the main direction of force, while the arrows 10 and 11 show the direction of force on the second and third sensors, respectively. On the second sensor 7, arranged on the outer side of the femur 5, the forces are directed towards the outer ends of the sensor, as indicated by the arrows 10. On the third sensor 8, arranged on the inner side of the femur 5, the forces are directed towards the middle point of the sensor, as indicated by the arrows 11.

FIG. 2 illustrates the stress S levels at the various sensors in function of time T for the hip implant according to the first embodiment. The time T is thus indicated on the horizontal axis and the stress S on the vertical axis, the upper half of the Figure indicating the tension stress and the lower half the compression stress. The hatched line 21 illustrates the stress measurement from the first sensor 6, which is arranged on the axis of the femoral stem, and thus remains stable and forms the reference. The upper curve 22 illustrates the stress measurements of the second sensor 7 and the lower curve 23 illustrates the stress measurements of the third sensor 8. During an initial phase, illustrated by the hatched area 24, the implant is not yet firmly attached to the femur, but as the curves 22 and 23 show, osseointegration takes place when time T advances, and the curves 22 and 23 reach a plateau level. In case osteolysis occurs and the implant loosens, the curves 22 and 23 illustrate this in the hatched area 25.

Figure 3:
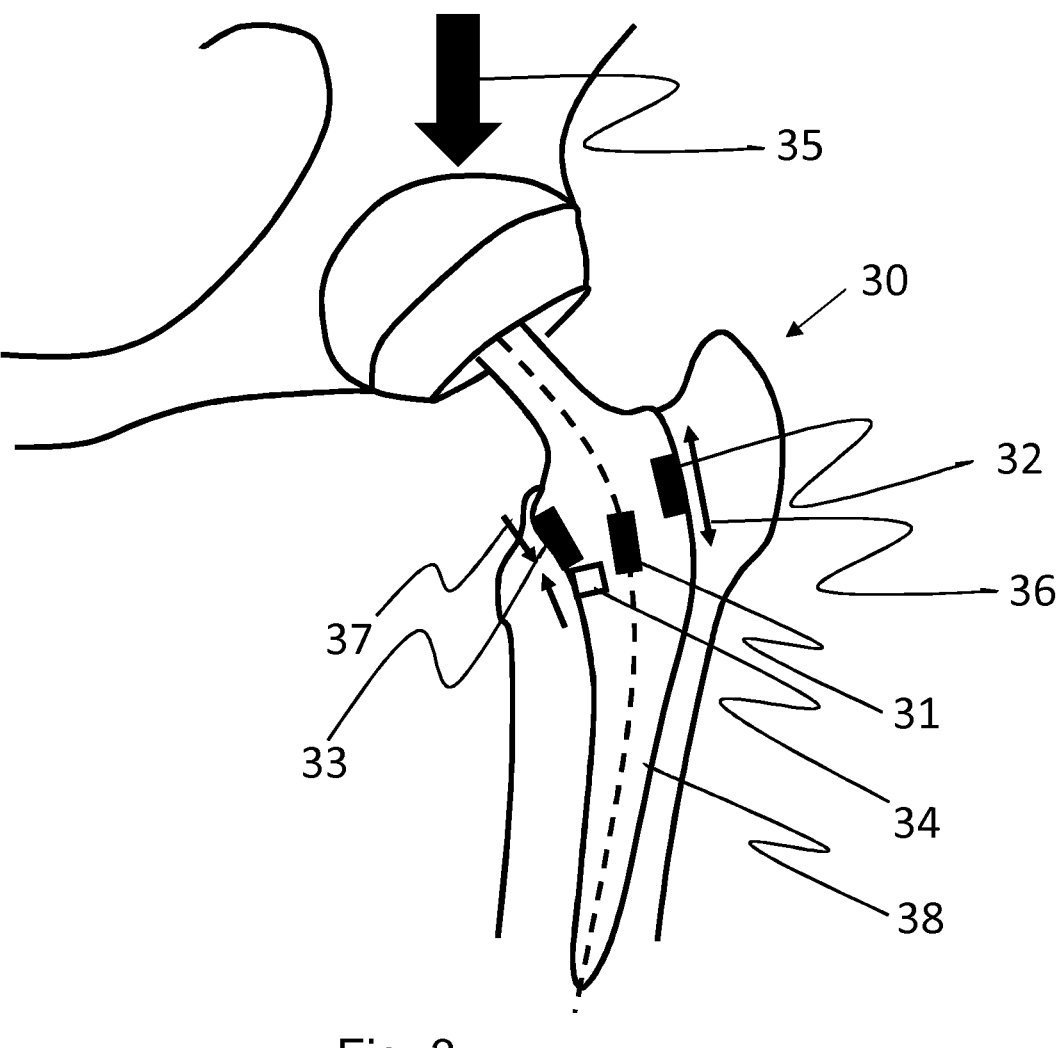
FIG. 3 schematically shows a hip implant according to a second embodiment.

FIG. 3 schematically shows a hip implant 30 according to a second embodiment. The hip implant 30 comprises, in connections with a structural part 38 (a fem oral stem) a first stress level sensor 31 is arranged on the axis of the femoral stem to indicate a reference stress level. A second stress level sensor 32 is arranged on the surface of the femoral stem, on the lateral side. A third stress level sensor 33 is arranged also on the surface of the femoral stem, but diametrically opposed to the second sensor 32, i.e. on the medial side. A fourth pH sensor 34, is arranged on the surface of the implant, in this embodiment near the third sensor 33. The arrows 35, 36 and 37 illustrate the directions of force as in FIG. 1.

Figure 4:
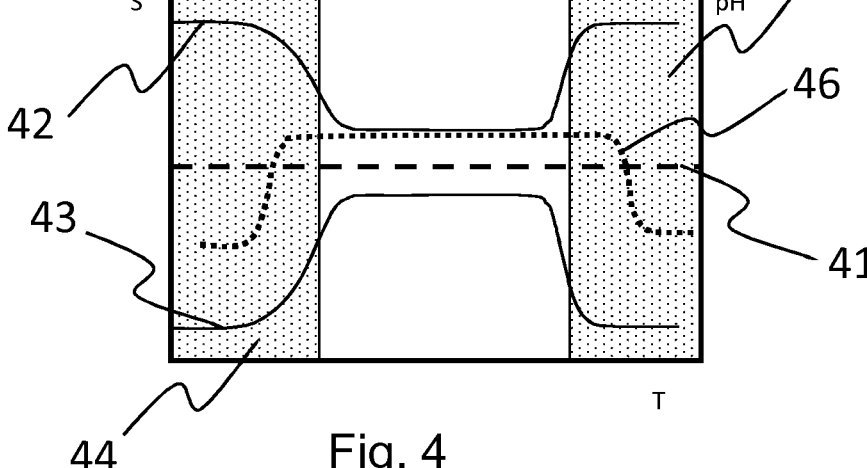
FIG. 4 illustrates the stress levels at the various sensors in function of time for the hip implant according to the second embodiment.

FIG. 4 illustrates the stress levels S at the various sensors in function of time T for the hip implant according to the second embodiment, as well as the changes in pH within the interface between the implant and the surrounding bone. The time T is thus indicated on the horizontal axis and the stress S and the pH on the vertical axes, the upper half of the Figure indicating the tension stress and the lower half the compression stress. The hatched line 41 illustrates the stress measurement from the first sensor 31, which is arranged on the axis of the femoral stem, and thus remains stable and forms the reference. The upper curve 42 illustrates the stress measurements of the second sensor 32 and the lower curve 43 illustrates the stress measurements of the third sensor 33. The hatched curve 46 illustrates the pH measurement from the pH sensor (fourth sensor) 34. During an initial phase, illustrated by the hatched area 44, the implant is not yet firmly attached to the femur, but as the curves 42 and 43 show, osseointegration takes place when time T advances, and the curves 42 and 43 reach a plateau level. In case osteolysis occurs and the implant loosens, the curves 42 and 43 illustrate this in the hatched area 45. The effect of change in pH is also shown with the curve 46, as osteolysis also has an effect of lowering the pH, as infections or inflammation may occur.

Figure 5:
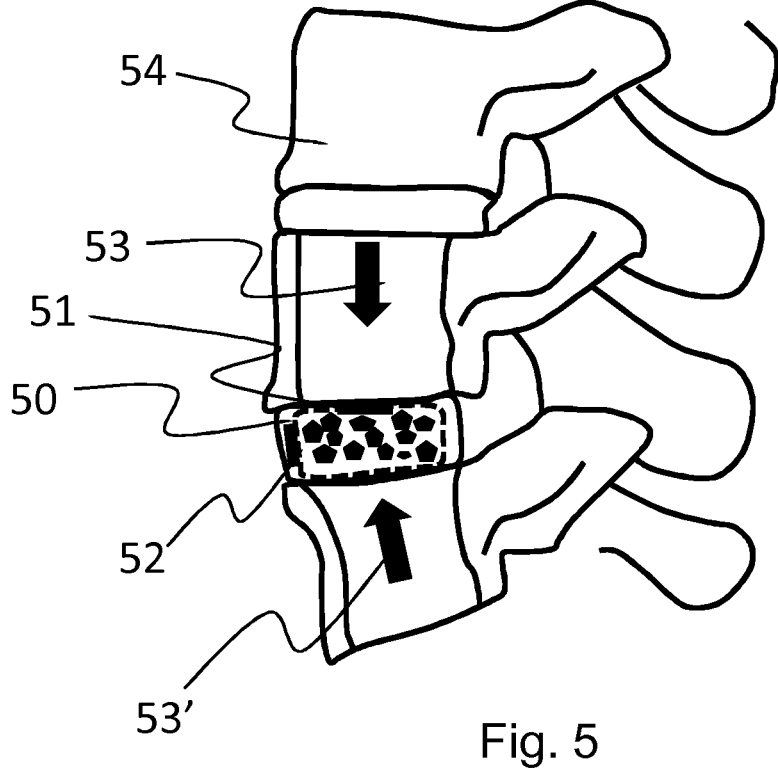
FIG. 5 schematically shows a spinal implant according to a third embodiment.

FIG. 5 schematically shows a spinal implant 50 according to a third embodiment. The spinal implant is here an intervertebral disc 50 arranged between vertebral bodies 54. The spinal implant 50 comprises two sensors 51 and 52, of which the first sensor 51 is arranged to be essentially in contact with a vertebral body and the second sensor 52 is arranged on the side of the implant, on the distal side of the spine. The arrows 53 and 53' illustrate the direction of force that is applied on the spinal implant 50.

Figure 6:
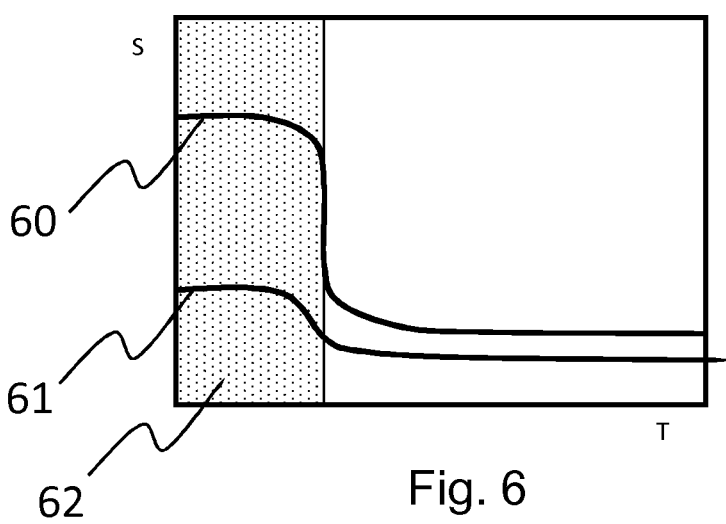
FIG. 6 illustrates the stress levels at the various sensors in function of time for the spinal implant according to the third embodiment.

FIG. 6 illustrates the stress S levels at the various sensors in function of time T for the spinal implant according to the third embodiment. The time T is thus indicated on the horizontal axis and the stress S on the vertical axis, the upper half of the Figure indicating the compression stress and the lower half the shear stress. The upper curve 60 illustrates the stress measurement from the first sensor 51 and the lower curve 61 illustrates the stress measurements of the second sensor 52. During an initial phase, illustrated by the hatched area 62, the implant is not yet firmly attached to the vertebral bodies, but as the curves 60 and 61 show, osseointegration takes place when time T advances, and the curves 60 and 61 reach a plateau level.

Figures 7, 8:
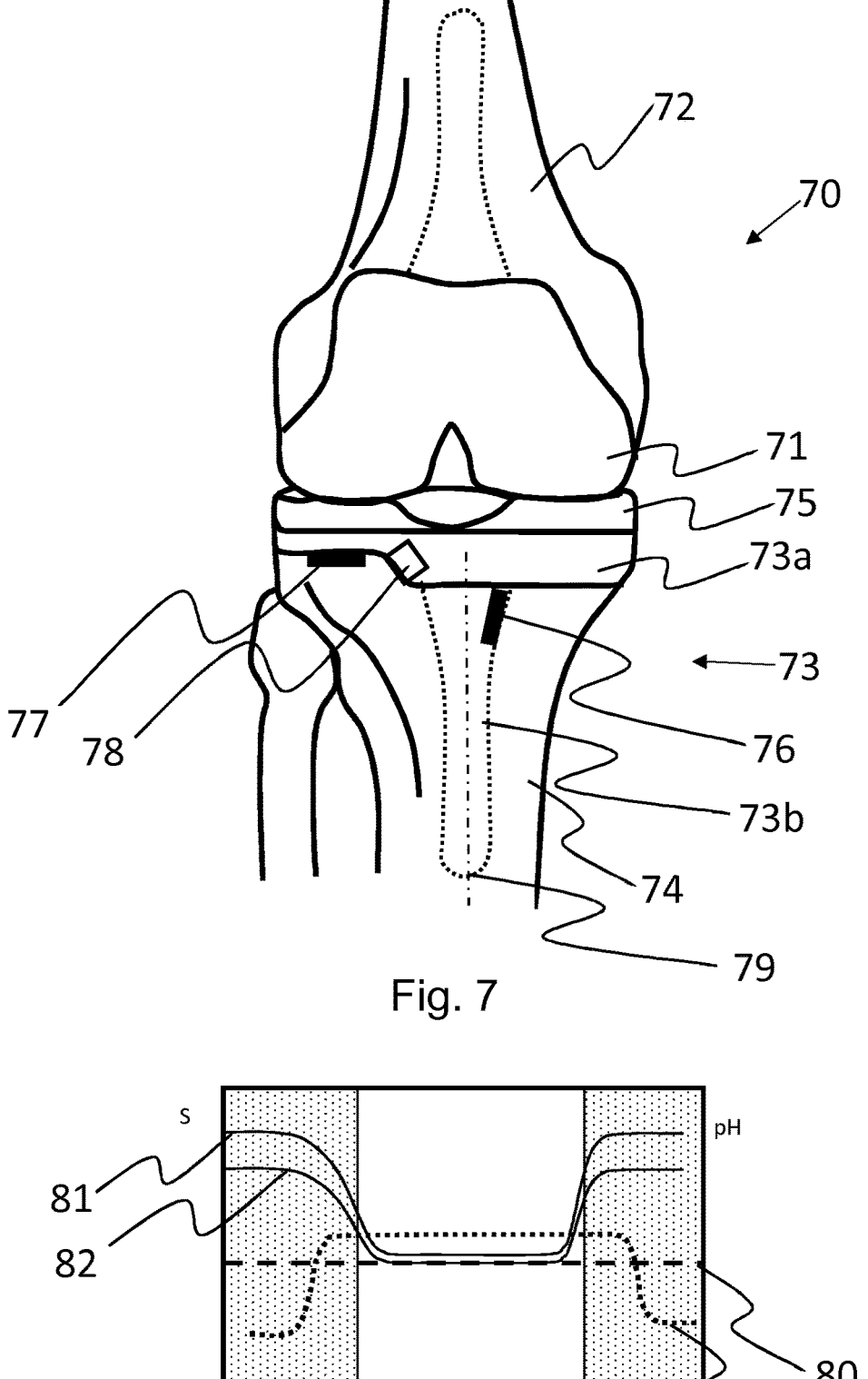
FIG. 7 schematically shows a knee implant according to a fourth embodiment.
FIG. 8 illustrates the stress levels at the various sensors in function of time for the knee implant according to the fourth embodiment.

FIG. 7 schematically shows a knee implant 70 according to a fourth embodiment. The knee implant 70 is a total knee prosthesis, comprising a femoral component 71 attached to the femur 72, a tibial component 73 attached to the tibia 74, as well as a spacer 75. The tibial component 73 (structural part) comprises a base plate 73a and a stem 73b, the stem defining a tibial axis 79. The tibial component 73 comprises three sensors, a first stress level sensor 76, a second stress level sensor 77 and a third pH sensor 78. The first sensor 76 is arranged on the surface of the stem 73b essentially in line with the tibial axis 79. The second sensor 77 is arranged on the surface of the base plate 73a, facing towards the tibia, i.e. away from the femur. The pH-sensor (third sensor) 78 is arranged within the base plate 73a, close to the outer surface of it.

FIG. 8 illustrates the shear stress S levels at the various sensors in function of time T for the knee implant according to the fourth embodiment. The Figure also shows the variations of pH, as measured by the third sensor 78. The time T is thus indicated on the horizontal axis and the stress S and the pH on the vertical axes. The hatched line 80 illustrates a reference level, i.e. neutral axis for stress. The uppermost curve 81 illustrates the stress measurements of the second sensor 77 and the middle curve 82 illustrates the stress measurements of the third sensor 78. The hatched curve 83 illustrates the pH measurement from the pH sensor (third sensor) 78. During an initial phase, illustrated by the hatched area 844, the implant is not yet firmly attached to the femur, but as the curves 81, 82 and 83 show, osseointegration takes place when time T advances, and the curves 81, 82 and 83 reach a plateau level. In case osteolysis occurs and the implant loosens, the curves 84, 82 and 83 illustrate this in the hatched area 85.

The invention claimed is:

1. An implant comprising
a non-metallic structural part made of a fibre reinforced composite, having isoelastic properties with bone,
a reference stress level sensor arranged in connection with the structural part,
a first osseointegration level sensor arranged on a surface of the structural part, and capable of becoming attached to the bone during osseointegration of the implant, which second osseointegration level sensor is a stress level sensor; and
a second osseointegration level sensor capable of becoming attached to the bone during osseointegration of the implant, wherein the first osseointegration level sensor and/or second osseointegration level sensor are capable of bioactive attachment to the bone during osseointegration of the implant; and, optionally, wherein the second osseointegration level sensor is diametrically opposed to the first osseointegration level sensor.

2. The implant according to claim 1, wherein the second osseointegration sensor is a stress level sensor.

3. The implant according to claim 1, wherein each of the reference sensor, the first osseointegration level sensor and the second osseointegration level sensor are selected from a group consisting of stress gauge, microelectromechanical sensor, piezoresistive sensor and passive resonator based sensor.

4. The implant according to claim 1, wherein the implant further comprises a biochemical sensor arranged on the surface of the structural part.

5. The implant according to claim 4, wherein the biochemical sensor is a pH sensor.

6. The implant according to claim 1, wherein the implant is a fracture fixation plate, a femoral stem of a hip prosthesis, a hip prosthesis, a knee prosthesis, an intramedullary nail, a vertebral fusion implant, plastic surgery implant, a jawbone implant, a cranial implant, a dental implant or a distractor.

7. The implant according to claim 1, wherein the implant is a hip prosthesis, wherein
the first structural part is femoral stem,
the reference stress level sensor is arranged inside the femoral stem, on the axis of the femoral stem,
the first osseointegration level sensor is arranged on the surface of the femoral stem, on its lateral side, and
the second osseointegration level sensor is arranged on the surface of the femoral stem, on its medial side.

8. The implant according to claim 7, further comprising a second structural part which is an acetubular cup.

9. The implant according to claim 1, wherein the implant is an intervertebral disc, wherein
the reference stress level sensor is arranged on a first surface of the structural part, the first surface being a lateral distal surface of the structural part, and the first osseointegration level sensor is arranged on a second surface of the structural part, the second surface being arranged to face a vertebral body (54).

10. The implant according to claim 1, wherein the implant is a knee prosthesis, wherein the first structural part is tibial component comprising a tibial base plate, and a tibial stem, the tibial stem defining a tibial axis, the reference stress level sensor is arranged on the surface of the tibial stem, essentially parallel to the tibial axis, the first osseointegration level sensor is arranged on the surface of the tibial base plate, the surface being essentially perpendicular to the tibial axis, on a lateral side, facing away from the tibial base plate, and an optional pH sensor is arranged on the surface of the tibial base plate, the surface being at an angle different from 90° with respect to the tibial axis.

11. The implant according to claim 10, further comprising a second structural part which is a femoral component and a third structural part which is a spacer.

12. An implant system comprising an implant according to claim 1, and at least one processing core and memory comprising computer executable instructions, the computer executable instructions being configured to, together with the memory and the at least one processing core, cause the implant system to process the measurement results received from the sensors.

13. The implant system according to claim 12, wherein at least one processing core and memory comprising computer executable instructions are comprised in a mobile device.

14. The implant system according to claim 13, wherein the mobile device is configured to transmit results of the processing of the measurement results to a database, and to raise an alarm in case of change in the results of analysis.

\*    \*    \*    \*    \*